United States Patent [19]

Inagi et al.

[11] Patent Number: 5,376,107
[45] Date of Patent: Dec. 27, 1994

[54] ELECTROTHERAPEUTIC DEVICE

[75] Inventors: Toshio Inagi, Mishima; Toyojiro Muramatsu, Shizuoka; Hidetaka Nagai, Hachioji; Kazuo Murata, Takatsuki; Kenichi Takeuchi, Takatsuki; Shuichi Izuchi, Takatsuki, all of Japan

[73] Assignees: Kowa Co., Ltd., Nagoya; Yuasa Battery Co., Ltd., Takatsuki, both of Japan

[21] Appl. No.: 965,618

[22] Filed: Oct. 22, 1992

Related U.S. Application Data

[63] Continuation of Ser. No. 664,663, Mar. 5, 1991, abandoned.

[30] Foreign Application Priority Data

Mar. 5, 1990 [JP] Japan ................................ 2-53153

[51] Int. Cl.$^5$ ................................ A61N 1/30
[52] U.S. Cl. .............................. 607/75; 604/20; 607/152
[58] Field of Search ............... 607/115, 152, 2, 75; 604/20; 429/104, 127, 162, 191, 192

[56] References Cited

U.S. PATENT DOCUMENTS

| Re. 31,489 | 1/1984  | Sekido et al. .............. 429/191 |
| 4,141,359  | 2/1979  | Jacobsen et al. ........... 604/20  |
| 4,211,222  | 7/1980  | Tapper ....................... 604/20  |
| 4,619,252  | 10/1986 | Ibbott ........................ 604/20  |
| 4,764,438  | 8/1988  | Vaughn et al. .                     |
| 4,927,408  | 5/1990  | Haak et al. ................ 604/20  |
| 5,019,467  | 5/1991  | Fujiwara .................... 429/162 |
| 5,047,007  | 9/1991  | McNichols et al. ....... 604/20  |
| 5,080,646  | 1/1992  | Theeuwes et al. ........ 128/798 |

FOREIGN PATENT DOCUMENTS

| 0225556  | 6/1987  | European Pat. Off. . |
| 0240593  | 10/1987 | European Pat. Off. . |

Primary Examiner—Lee S. Cohen
Assistant Examiner—Brian L. Casler
Attorney, Agent, or Firm—Oblon, Spivak, McClelland, Maier & Neustadt

[57] ABSTRACT

An electrotherapeutic device for passing a DC electric current through a living organism by applying a voltage to the living organism includes a battery with an internal resistance which is high enough so that changes in the resistance value of the living organism can be disregarded. Excessive flow of current is avoided even when the resistance of the living organism fluctuates. The device is safe, easy to handle, and inexpensive. It is particularly suited for use with iontophoresis; a technology by which drugs are administered using electricity.

12 Claims, 2 Drawing Sheets

ELECTROTHERAPEUTIC DEVICE

This application is a continuation of application Ser. No. 07/664,663, filed on Mar. 5, 1991, now abandoned.

BACKGROUND OF THE INVENTION

1. Field of the Invention

The present invention relates to an electrotherapeutic device for passing a DC electric current through a living organism, and, in particular, to an easily handled electrotherapeutic device which produces no excessive flow of current even if the resistance of the living organism fluctuates.

2. Description of the Background Art

Many and various types of electrotherapeutic devices for passing electric current through a living organism are commonly known, mainly for use in medical treatment. They are broadly grouped into those for obtaining therapeutic effects from the passage of the electricity itself, which are used for the needle treatment and the like, and those for obtaining a therapeutic effect by injecting a drug into the living organism by means of the passage of electricity; a therapeutic method called iontophoresis.

Iontophoresis is a technology by which drugs are administered electrically for intracutaneous absorption. Iontophoresis have conventionally been considered to be effected by the mechanism in which the drugs are first ionized by the application of electricity, then absorbed intracutaneously. There are, however, the cases in which drugs are absorbed without prior ionization, and in which drugs are absorbed from both positive and negative electrodes. Many points remain to be theoretically elucidated about the mechanism of iontophoresis.

Intracutaneous electrical devices present some problems such as side effects which accompany the application of electricity, including shock, pain, burns, and the like. It is believed that these side effects occur because the resistance of the skin and the like fluctuates when electricity is passed through an organism so that the flow of current is greater than required, and also because the current density becomes localized from inadequate adhesion of the electrode pad to the skin.

A method conventionally adopted as a countermeasure to the above problem areas is providing a current regulating means such as an external resistance, a switch, or the like.

However, in all these countermeasures the current regulating means are separately provided outside of the power supply source for controlling the electric current. The device therefore becomes large and difficult to handle. An additional problem is nuisance involved in manipulating the current control device. For these reasons, it is difficult for the patient himself to use such a device, making it necessary for him to go to a hospital for treatment by a doctor.

Accordingly, the development of an electrotherapeutic device for passing an electric current through a living body which is safe, with no excess current flow, easy to handle, and also inexpensive has been eagerly awaited.

SUMMARY OF THE INVENTION

An object of the present invention is to provide, with due consideration to the drawbacks of such conventional devices, an electrotherapeutic device which is safe, has no excess current flow, is easy to handle, and is inexpensive.

The inventors of the present invention, as a result of intensive research, have discovered that the above problems could be eliminated by increasing the internal resistance of a battery itself to such an extent that the changes in the resistance of the skin can be disregarded. In addition, the inventors have discovered that the use of a solid electrolyte in the battery is most effective.

Accordingly, an object of the present invention is to provide in an electrotherapeutic device for passing an electric current through a living organism by applying a voltage to the living organism, a device characterized by comprising a battery with an internal resistance with high impedance of a degree that the changes in the resistance value of the living organism can be disregarded.

BRIEF DESCRIPTION OF THE DRAWINGS

These and other objects, features, and advantages of the present invention will become more apparent from the following description of the preferred embodiments taken in conjunction with the accompanying drawings, in which.

DETAILED DESCRIPTION OF THE INVENTION AND PREFERRED EMBODIMENTS

Figure 1:
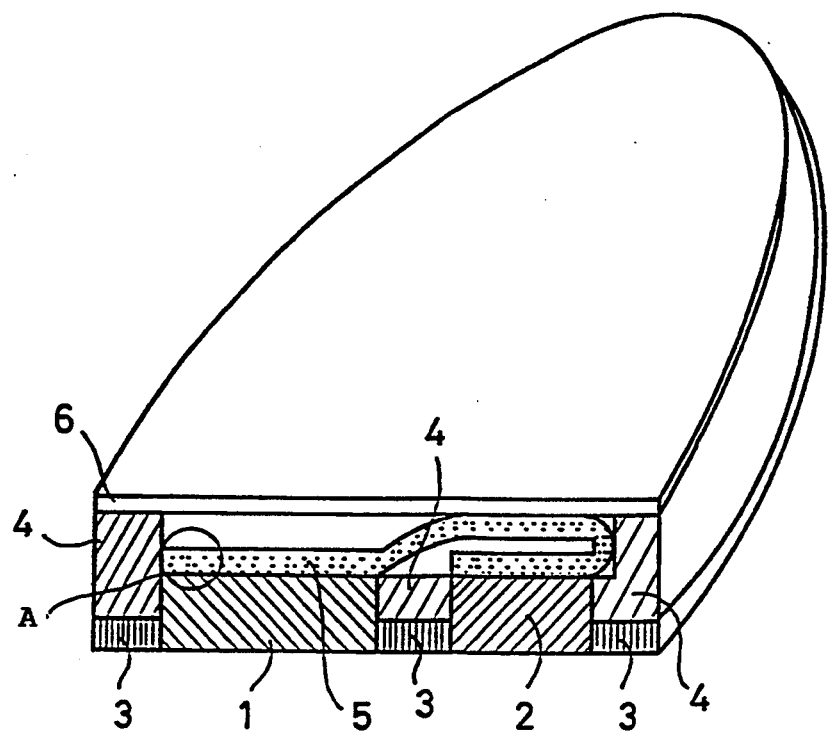
FIG. 1 is a cross-sectional view showing an embodiment of an electrotherapeutic device of the present invention.

As a means of providing an internal resistance with a high impedance, a method can be given, for example, in which a high impedance material is used as an electrolyte.

Here, as this type of electrolyte, a solid electrolyte is desirable because it normally has a high impedance and does not leak. Either an organic or inorganic solid electrolyte can be used for the purpose of the present invention. Examples which can be given of suitable organic solid electrolytes are polyether polymers, such as polyethylene oxide, polypropylene oxide, random copolymers of ethylene oxide and propylene oxide, and the like, polyester polymers, polyimine polymers, and the like.

Alkali metal salts such as $LiCF_3SO_3$, $LiClO_4$, and the like are normally used as supporting salts in combination with these organic solid electrolytes. Given as examples of inorganic solid electrolytes are $LiI$, $Li\text{-}\beta Al_2O_3$, $Li_3N$, $Li\text{-}Al_2O_3$, and the like.

A sheet-type battery utilizing a solid electrolyte is desirable, because it can provide excellent flexibility and superior adhesion between the electrode pad and the skin, is easy to handle, and can be manufactured at a low cost.

The insulators, conductive parts (current collectors), electrodes, insulating supports, skin-adhering parts, and the like used in the device of the present invention are the same as those used in a conventional electrotherapeutic device.

Silicone, natural rubber, vinyl chloride, and the like are examples of materials which can be used as insulators.

Examples of current collectors which can be used include foils of aluminum, copper, platinum, gold, and the like, carbon films, conductive fibers, conductive polymers, and the like.

Electrodes which can be used include manganese dioxide and the like for the positive electrode, and lithium, carbon, and the like for the negative electrode.

Examples which can be given of material for a conductive skin-adhering pad include acrylic resins such as sodium polyacrylate, polyvinylpyrrolidone, agar-agar, gelatine, methacrylic acid-methylmethacrylate copolymer, methylmethacrylate-butylmethacrylate-dimethylaminoethyl methacrylate copolymer, and the like. When these materials are to be impregnated with a drug, the material should be selected taking its affinity and compatibility with the drug into consideration.

When the present invention is used to pass an electric current through a living organism, the amperage must be in a range in which there are no harmful effects to the living organism. Although the range which is safe for the organism depends on the length of time during which the current is applied, generally 0.5 mA/cm$^2$ and lower is desirable. When consideration is given to effectiveness, a range from 0.005 to 0.25 mA/cm$^2$ is particularly desirable. It is necessary that the internal resistance be adjusted to a high impedance so that this current range is not exceeded, even in the case where the resistance of the living organism fluctuates during the passage of electricity. Specifically, the internal resistance of the battery should be adjusted so that the voltage is in the 1 to 12 V range and the amperage is in the 0.05 to 25 mA range over the entire device. The length of time during which the flow of electricity is applied should be less than one hour per application, with thirty minutes as a particularly desirable period of application. This time length can be suitably set by adjusting the discharge time of the solid electrolyte battery.

Types of drugs which can be administered by iontophoresis using the device of the present invention include indomethacin, flufenamic acid, flurbiprofen, dantrolene, nipragilol, propranolol, calcitonin, elcatonin, insulin, methylprednisolone, lidocaine, and the like. This method can be used in the treatment of patients suffering from shingles, rheumatism, myalgia, circulatory obstruction, osteoporosis, diabetes, and the like.

Because the internal resistance of the battery used with the electrotherapeutic device of the present invention has a high impedance, an excess current cannot flow, even when the resistance of the skin and the like fluctuates during the passage of electricity. Because a solid electrolyte is used, leakage of liquid from the battery is avoided. The use of a battery in sheet form provides superior adhesion to the skin, and, in addition, side effects such as burns and the like, caused by localization of the current density, can be prevented.

Furthermore, switches and the like are unnecessary, so the resulting simple structure of the device makes handling easy. For example, the device can be provided with an adhesive portion which is to be attached to the skin-adhering surface and a liner covering the adhesive and other portions. When the device is to be used, the liner is simply peeled off and the device is attached to the skin surface. This operation can be carried out very simply by the patient himself. In addition, it is possible to provide the device at a sufficiently low cost to be disposable.

Other features of this invention will become apparent in the course of the following description of exemplary embodiments which are given for illustration of the invention and are not intended to be limiting thereof.

EXAMPLES

Now referring to FIG. 1, this embodiment of a electrotherapeutic device of the present invention comprises a conductive skin-adhering pad 1 formed from a conductive polymer impregnated with a drug, a conductive skin-adhering pad 2 which is not impregnated with a drug, a nonconductive adhesive layer 3 which can adhere to a living organism, a support member 4 made of an insulating resin, a film-shaped battery 5, and a facing 6.

Figure 2:
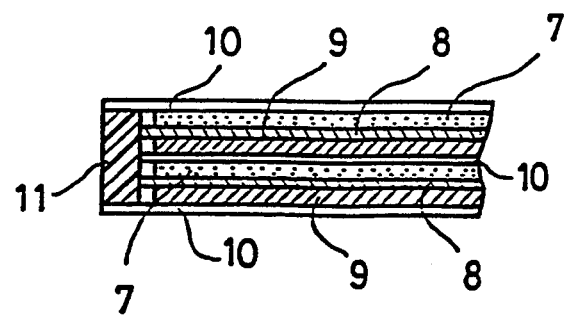
FIG. 2 is an enlarged cross-sectional view showing an embodiment of a solid organic electrolyte battery, the portion designated as "A" in FIG. 1.

FIG. 2 is a view showing an embodiment of a film battery used in the electrotherapeutic device of the present invention.

The battery comprises a positive electrode 7 fabricated from manganese dioxide, an organic solid electrolyte 8, a negative electrode 9 fabricated from lithium, a current collector 10 fabricated from aluminum, and a sealing port sealing layer 11 fabricated from a polyolefin resin and heat-fused to the current collector 10.

The organic solid electrolyte 8 was prepared in the following manner. Specifically, 10 parts by weight of a trifunctional polyether of 3,000 molecular weight formed by random copolymerization of ethylene oxide and propylene oxide in an 8:2 ratio; 1 part by weight of modified liquid MDI (methylenediphenylene diisocyanate); and 0.8 parts by weight of 1,4-diazabicyclo(2,2,-2)octane, to which were added 1.3 parts by weight of LiCF$_3$SO$_3$ as a supporting salt were uniformly blended, then melted and cast on a glass plate and reacted for 2 hours at 80° C. in a nitrogen atmosphere to provide a film-shaped, solid electrolyte with a thickness of 100 $\mu$m. The ion conductivity of the film when measured by the complex impedance method was $3 \times 10^{-6}$ S·cm$^{-1}$ at 25° C. This organic solid electrolyte was also used as a binding agent for the active material in the positive electrode 7.

The film-shaped battery of FIG. 2, which has an electrode area of 10 cm$^2$ and an internal resistance of 2 k $\Omega$, was incorporated into the electrotherapeutic device of FIG. 1 provided with a pad with an area of 100 cm$^2$ in contact with the skin. The final assembly was tested by applying an electric current for 1 hour. The current passing through the skin was less than 2 mA. No adverse effects on the skin, such as burns or the like, were observed.

Figure 3:
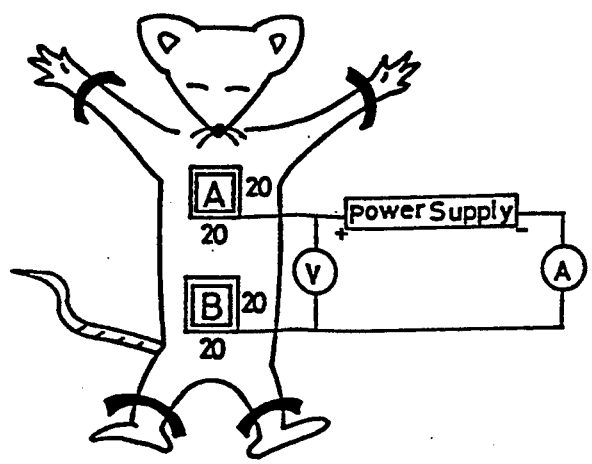
FIG. 3 is a circuit diagram of an experiment using a rat.

A test system was constructed according to the circuit diagram of FIG. 3 for use with experimental rats.

Two sheets of non-woven fabric, 4 cm$^2$ in area, were prepared. One sheet was impregnated with 0.5 ml of physiological saline solution to be used as a pad A. The other sheet was impregnated with 0.5 ml of a 50% ethanol and water solution (pH 6) containing 1% indomethacin, to be used as a pad B.

The pad A and the pad B, separated by 1 cm, were applied to the skin of the shaven abdomen of a rat. A sheet of aluminum foil was secured to each of the pads. A positive electrode was connected to the pad A and a negative electrode to the pad B. The voltage was monitored on a voltmeter V and the amperage on an ammeter A.

A fixed current was set to pass through the experimental subject

<Skin irritation>

For each measured amperage the subject was monitored visually for the occurrence of burns over an elapsed time. The results are shown in Table 1.

TABLE 1

| Current | Elapsed time (minutes) | | | | | |
|---|---|---|---|---|---|---|
| (mA/cm²) | 5 | 10 | 15 | 30 | 45 | 60 |
| 0 | — | — | — | — | — | — |
| 0.05 | — | — | — | — | — | — |
| 0.075 | — | — | — | — | — | — |
| 0.125 | — | — | — | ± | + | + |
| 0.25 | — | — | ± | + | + | + |

— : No change.
± : Small burns were observed.
+ : Obvious burns were observed.

<Measurement of skin resistance>

For each measured amperage, the voltage between the pads A and B was measured 15 minutes after the initial application of electricity to calculate the skin resistance.

The results are shown in Table 2.

TABLE 2

| Current (mA/cm²) | Voltage after 15 min. (V) | Resistance after 15 min. ($\Omega \times 10^3$) |
|---|---|---|
| 0.05 | 1.70 | 8.50 |
| 0.075 | 1.60 | 5.33 |
| 0.125 | 2.50 | 5.00 |
| 0.25 | 2.63 | 2.63 |

<Progress of the concentration of drug absorbed in blood plasma>

For each measured amperage the concentration of indomethacin absorbed in the blood plasma was measured versus elapsed time.

Figure 4:
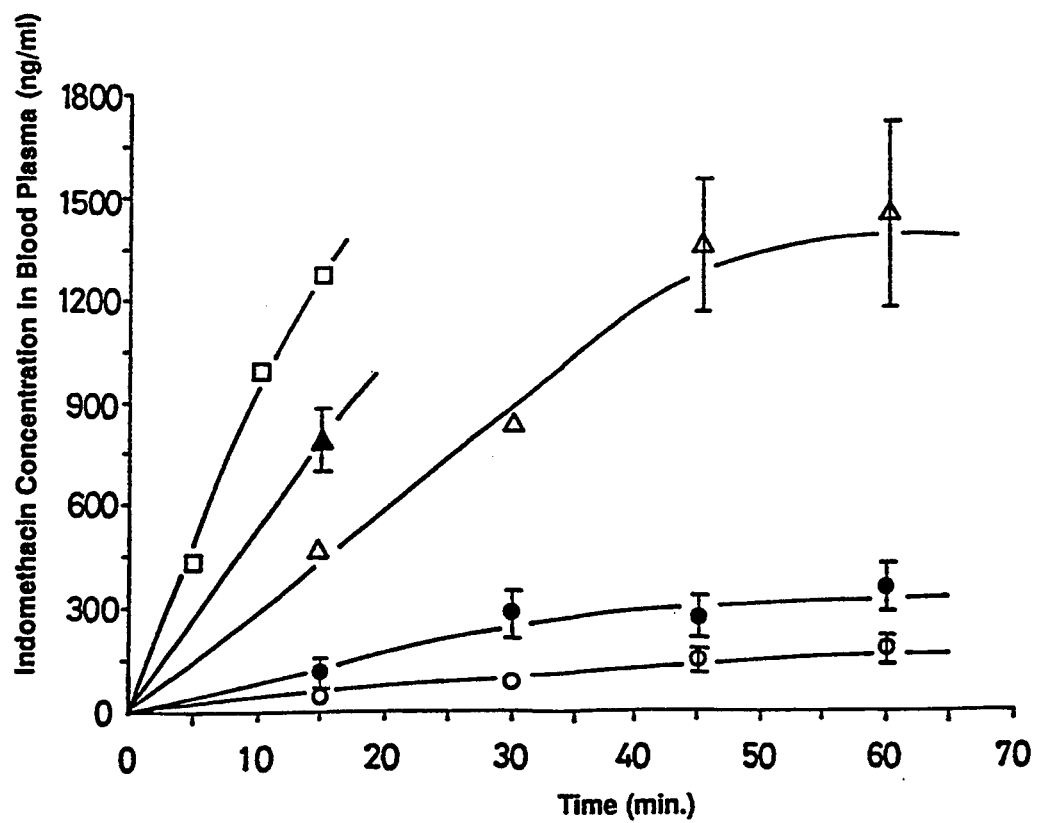
FIG. 4 is a graph showing the progress of the concentration of indomethacin absorbed in the blood plasma.

The results are shown in FIG. 4, in which the curves connected by open circles, solid circles, open triangles, solid triangles, and open squares represent those obtained by measured amperages of 0 mA, 0.2 mA, 0.3 mA, 0.5 mA, and 1.0 mA, respectively.

Obviously, numerous modifications and variations of the present invention are possible in light of the above teachings. It is therefore to be understood that within the scope of the appended claims, the invention may be practiced otherwise than as specifically described herein.

What is claimed is:

1. An electrotherapeutic device for passing an electric current through a living organism in order to drive a drug into the organism, comprising:
    a battery, comprising means for providing a high internal resistance, said means for providing comprising a high electrical resistance solid electrolyte, said battery further comprising a first electrode and a second electrode which electrically connect to opposite sides of the solid electrolyte;
    a first contact pad connected to said first electrode, said first contact pad having a first surface for contact to said organism, said first surface having a first surface area, said first contact pad including means for holding a drug, wherein operation of the electrotherapeutic device administers the drug to the organism,
    a second contact pad connected to the second electrode, and
    wherein said high internal resistance is substantially provided by said solid electrolyte and said means for providing limits the average current density at said first contact pad to less than 0.5 mA per square centimeter.

2. A device according to claim 2, wherein said solid electrolyte has a conductivity of less than $10^{-5}$ S per cm.

3. A device according to claim 1, wherein the first electrode has first and second major surfaces and said solid electrolyte opposes the first major surface of said first electrode and the resistance per unit surface area of the second major surface of said first electrode is greater than 100 ohms per square centimeter.

4. A device according to claim 1, wherein said average current density is limited to less than 0.125 mA per cm².

5. A device according to claim 1, wherein a relationship exists between a voltage V provided by said battery, a resistance R of said solid electrolyte between said first electrode and said second electrode, a current density J at said first electrode and an area A of said first electrode of the form:

$$V \leq (J \times A) \times R$$

wherein J is equal to or less than 0.125 ma/cm².

6. A device according to claim 1, wherein:
    the battery electrodes comprise a member of the group consisting of manganese dioxide, lithium, and carbon.

7. A device according to claim 1, wherein:
    said first contact pad comprises an acrylic resin impregnated with a pharmaceutical drug.

8. A device according to claim 1, wherein said battery has a voltage between 1 and 12 volts and a total current of between 0.05 and 25 mA.

9. An electrotherapeutic device according to claim 1, wherein the solid electrolyte comprises a material that is selected from a member of the group consisting of organic high polymers and inorganics.

10. An electrotherapeutic device for passing an electric current through a living organism even when the electrical resistance of the living organism fluctuates, comprising:
    a first contact pad;
    a second contact pad;
    a battery, said battery comprising means for providing a high internal electrical resistance comprising a solid electrolyte, wherein said high internal electrical resistance is substantially provided by said solid electrolyte,
    a first electrode that is connected to the first contact pad,
    a second electrode that is connected to the second contact pad,
    wherein the first and second electrodes oppose one another across said solid electrolyte;
    wherein said first contact pad has a first surface for contact to said organism, said organism has a resistance to flow of current between the first contact pad and the second contact pad, and said first surface has a first surface area, said internal resistance of the battery is substantially greater than the resistance of the living organism, and said means for providing limits variations in current provided by the battery to said first contact pad, and limits the average current density provided by the battery at said first contact pad to less than 0.5 mA per square centimeter.

11. A device according to claim 15 wherein said solid electrolyte comprises a member selected from the group consisting of polyether polymers, polyester polymers, and polyamine polymers.

12. A device according to claim 10, wherein said solid electrolyte comprises lithium.

* * * * *

UNITED STATES PATENT AND TRADEMARK OFFICE
CERTIFICATE OF CORRECTION

PATENT NO. : 5,376,107
DATED : December 27, 1994
INVENTOR(S) : Toshio INAGI, et al.

It is certified that error appears in the above-indentified patent and that said Letters Patent is hereby corrected as shown below:

On the title page, Item [75], the last inventor's name is spelled incorrectly. It should read:

--Syuichi Izuchi--

Signed and Sealed this

Eighteenth Day of April, 1995

*Attest:*

BRUCE LEHMAN

*Attesting Officer*  *Commissioner of Patents and Trademarks*